US012773803B2

(12) United States Patent
Cannon et al.

(10) Patent No.: US 12,773,803 B2
(45) Date of Patent: Oct. 27, 2026

(54) MENISCAL DOVETAIL SLOT CONVERTER

(71) Applicant: Arthrex, Inc., Naples, FL (US)

(72) Inventors: Bryan Cannon, Miami, FL (US); Robert Benedict, Naples, FL (US); Shane Noble, Naples, FL (US); Brian J. Cole, Chicago, IL (US)

(73) Assignee: Arthrex, Inc., Naples, FL (US)

( * ) Notice: Subject to any disclaimer, the term of this patent is extended or adjusted under 35 U.S.C. 154(b) by 111 days.

(21) Appl. No.: 18/799,087

(22) Filed: Aug. 9, 2024

(65) Prior Publication Data

US 2025/0065527 A1 Feb. 27, 2025

Related U.S. Application Data

(60) Provisional application No. 63/520,684, filed on Aug. 21, 2023.

(51) Int. Cl.
*B26D 7/00* (2006.01)
*A61F 2/30* (2006.01)

(52) U.S. Cl.
CPC ........ *B26D 7/0006* (2013.01); *A61F 2/30756* (2013.01)

(58) Field of Classification Search
CPC .......... B26D 7/0006; B26D 7/01; A61B 17/15
See application file for complete search history.

(56) References Cited

U.S. PATENT DOCUMENTS 4,096,777 A * 6/1978 Adams ..................... B27G 5/02 83/762
4,320,678 A * 3/1982 Volk ..................... B23D 51/025 83/522.18
4,565,192 A * 1/1986 Shapiro .............. A61B 17/1604 606/88
5,105,862 A * 4/1992 Skinner .................... B23Q 1/74 144/287
5,415,663 A 5/1995 Luckman
5,483,858 A * 1/1996 Chen ...................... B23D 47/04 269/319
5,575,793 A * 11/1996 Carls .................. A61B 17/1767 606/88
5,730,434 A * 3/1998 Schoene ................. B25B 5/163 83/466
5,733,289 A * 3/1998 Seedhom ........... A61B 17/1677 606/80
6,962,592 B2 11/2005 Gatturna
8,549,970 B2 * 10/2013 Stone ................... B23D 45/042 83/490
8,707,560 B2 * 4/2014 Hess ...................... B25B 11/00 29/896.4
8,795,284 B2 8/2014 Ribeiro
12,478,384 B2 * 11/2025 Evans ................ A61B 17/1635
2013/0096680 A1 4/2013 Ribeiro
2016/0270933 A1 9/2016 Bosworth
2022/0117758 A1 4/2022 Rodriguez
2023/0218403 A1 7/2023 Noble

FOREIGN PATENT DOCUMENTS

CN 102636370 A 8/2012
CN 106353127 A 1/2017
CN 207448538 U 6/2018

* cited by examiner

*Primary Examiner* — Sean M Michalski

(74) *Attorney, Agent, or Firm* — McDonnell Boehnen Hulbert & Berghoff LLP

(57) ABSTRACT

The present disclosure provides a meniscal allograft transplantation system and methods of use.

11 Claims, 2 Drawing Sheets

MENISCAL DOVETAIL SLOT CONVERTER

CROSS-REFERENCE TO RELATED APPLICATIONS

This application claims priority to U.S. Provisional Application No. 63/520,684 entitled "Meniscal Dovetail Slot Converter," filed on Aug. 21, 2023, the contents of which are hereby incorporated by reference in its entirety.

BACKGROUND

Meniscal allograft transplantation is a common technique for total replacement of a torn lateral or medial meniscus. Meniscal allografts have been found to be a feasible alternative in the effort to limit sequelae of arthritis that can occur with meniscal excision. One common type of meniscal allograft transplantation utilizes a trapezoidal bone block commonly known as a dovetail meniscal allograft. However, some surgeons prefer an alternative surgical technique requiring a meniscal allograft in the shape of a rectangular slot. As such, an improved system that converts the dovetail shape of the prepared meniscal allograft into a rectangular slot is desirable.

SUMMARY

The disclosure herein includes a meniscal allograft dovetail slot converter and methods of use.

In particular, in one aspect, the present disclosure provides a device for use in a meniscal allograft transplantation procedure. The device includes a base. The device also includes a first sidewall extending vertically from the base and a second sidewall extending vertically from the base. The second sidewall is spaced away from the first sidewall at a fixed distance. The device also includes a third sidewall extending vertically from the base. The third sidewall is coupled to the first sidewall and the second sidewall. The device also includes a locking member coupled to the second sidewall. The device also includes a removable cutting guide including a slotted through-hole. The removable cutting guide is configured to be removably coupled to the first sidewall and the second sidewall.

These as well as other aspects, advantages, and alternatives, will become apparent to those of ordinary skill in the art by reading the following detailed description, with reference where appropriate to the accompanying drawings.

DETAILED DESCRIPTION

Figure 1:
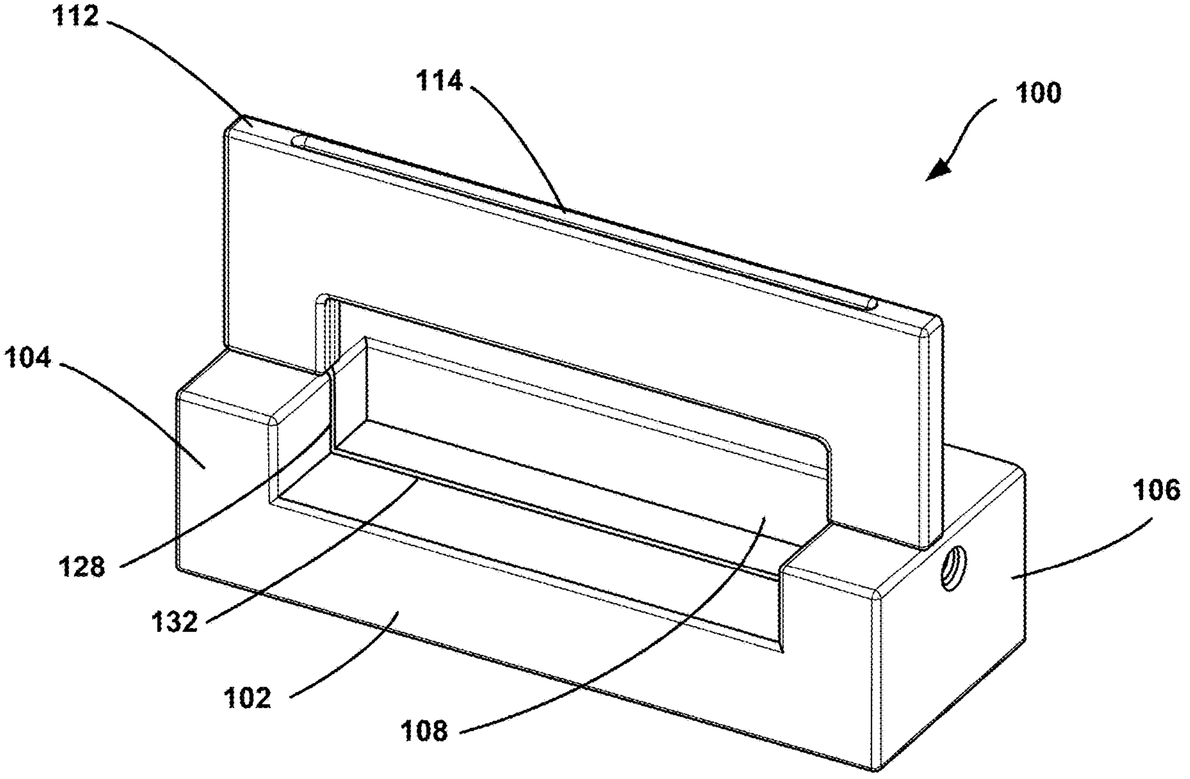
FIG. 1 is a perspective view of an example device for use in a meniscal allograft transplantation procedure.
Figure 2:
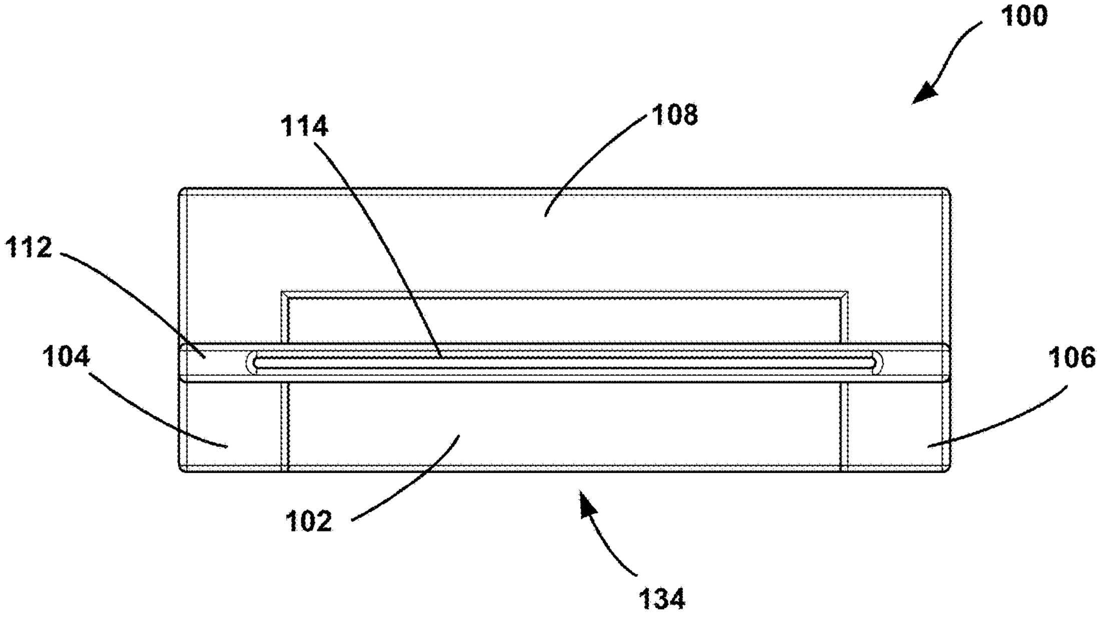
FIG. 2 is a top view of the example device of FIG. 1.

With reference to the Figures, FIGS. 1-4 illustrate a device 100 for use in a meniscal allograft transplantation procedure. As shown in FIGS. 1-4, the device 100 includes a base 102. The device 100 also includes a first sidewall 104 extending vertically from the base 102 and a second sidewall 106 extending vertically from the base 102. The second sidewall 106 is spaced away from the first sidewall 104 at a fixed distance. The device 100 also includes a third sidewall 108 extending vertically from the base 102. The third sidewall 108 is coupled to the first sidewall 104 and the second sidewall 106. In one example, the third sidewall 108 is perpendicular to both the first sidewall 104 and the second sidewall 106. The device 100 also includes a locking member 110 coupled to the second sidewall 106. The device 100 also includes a removable cutting guide 112 including a slotted through-hole 114. The removable cutting guide 112 is configured to be removably coupled to the first sidewall 104 and the second sidewall 106.

Figure 3:
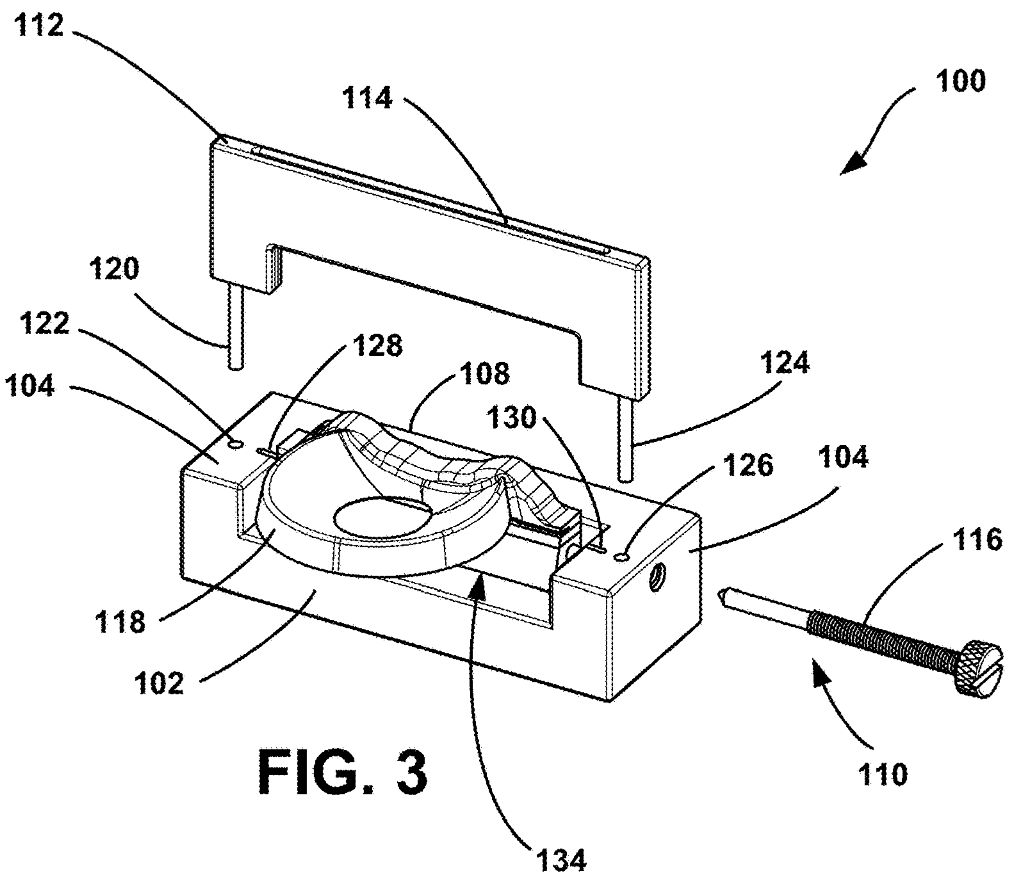
FIG. 3 is a perspective view of the device of FIG. 1 with a meniscal allograft positioned thereon.
Figure 4:
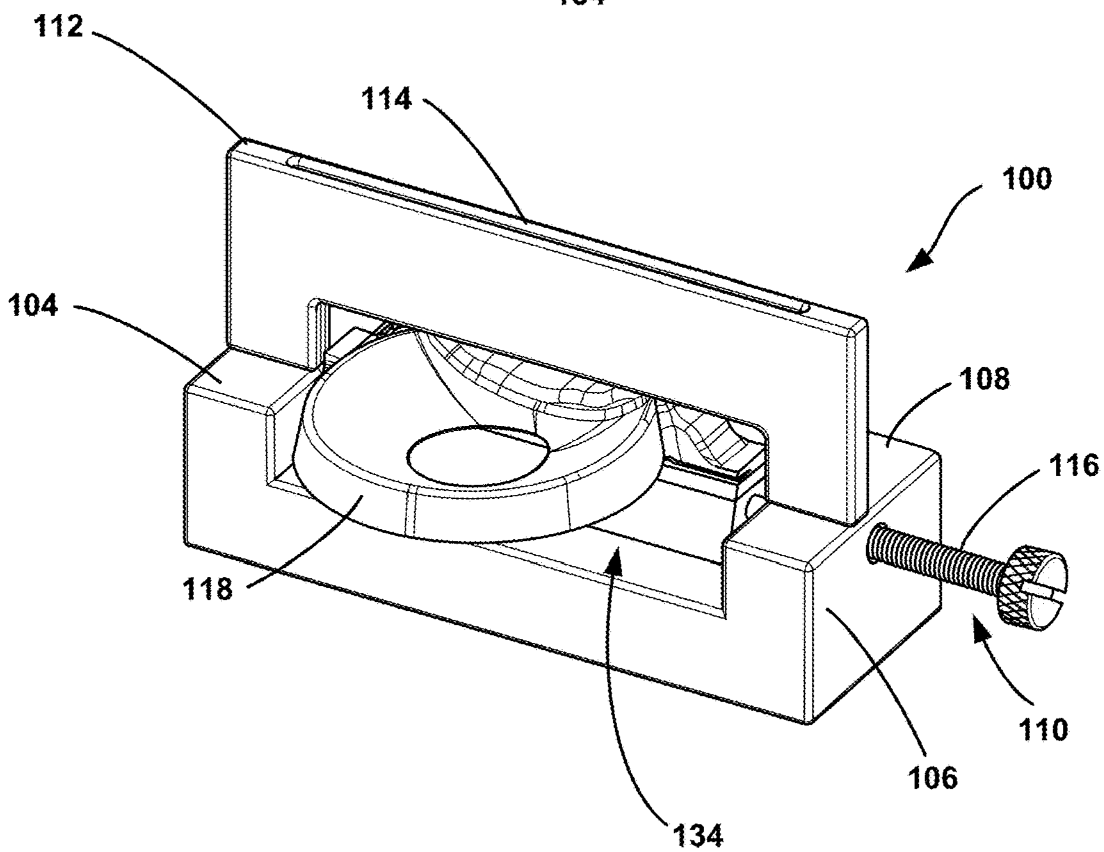
FIG. 4 is a perspective view of the device of FIG. 1 with a meniscal allograft positioned therein.

In one example, as shown in FIGS. 3-4, the locking member 110 comprises a threaded rod 116. In such an example, rotation of the threaded rod 116 in a first direction moves the locking member 110 closer to the first sidewall 104, and rotation of the threaded rod 116 in a second direction moves the locking member 110 further from the first sidewall 104. In one example, a longitudinal axis of the threaded rod 116 is offset from the slotted through-hole 114. Such an arrangement ensures that when a saw is positioned through the slotted through-hole 114 to trim the meniscal allograft 118, the saw does not contact the threaded rod 116. In one particular example, the threaded rod 116 comprises a set screw with a first portion that is threaded and a second portion that is not threaded.

In one example, the device 100 includes a first locking member coupled to the first sidewall and a second locking member coupled to the second sidewall. In another example, the device includes a single locking member coupled to the first sidewall or the second sidewall.

In one example, the removable cutting guide 112 includes a first pin 120 configured to be positioned in a first hole 122 in the first sidewall 104, and the removable cutting guide 112 includes a second pin 124 configured to be positioned in a second hole 126 in the second sidewall 106.

In one example, a length of the slotted through-hole 114 is greater than the fixed distance between the first sidewall 104 and the second sidewall 106. In one such example, the first sidewall 104 includes a first groove 128 and the second sidewall 106 includes a second groove 130. The first groove 128 and the second groove 130 are vertically aligned with the slotted through-hole 114 when the removable cutting guide 112 is removably coupled to the first sidewall 104 and the second sidewall 106. In one such example, a distance from a bottom of the first groove 128 to a bottom of the second groove 130 is equal to the length of the slotted through-hole.

In one example, the slotted through-hole 114 comprises a first slotted through-hole, and the base 102 includes a second slotted through-hole 132. In such an example, the second slotted through-hole 132 is vertically aligned with the first slotted through-hole 114 when the removable cutting guide 112 is removably coupled to the first sidewall 104 and the second sidewall 106. Such an arrangement may help ensure that, when in use, a saw goes all the way through the meniscal allograft 118 positioned in the device 100. The second slotted through-hole 132 further enables easy removal of debris from the device 100 after use, since the debris can be flushed out through the second slotted through-hole 132.

In another example, the second slotted through-hole 132 is a groove in the base 102 that does not pass all the way through the base 102. Such a groove is vertically aligned with the slotted through-hole 114 when the removable cutting guide 112 is removably coupled to the first sidewall 104 and the second sidewall 106. Such an arrangement may help ensure that, when in use, a saw goes all the way through the meniscal allograft 118 positioned in the device 100.

In one example, the device 100 further includes an opening 134 opposite the third sidewall 108. The opening 134 may define an area to receive a meniscal allograft 118 when in use.

As described above, meniscal allografts have been found to be a feasible alternative in the effort to limit sequelae of arthritis that can occur with meniscal excision. Simplified graft preparation and recipient tibia preparation, to allow for the transplant to be positioned anatomically and anchored with reliable fixation, is the ultimate goal of the procedure. The meniscal allograft includes two components: the lateral meniscus allograft and the bone bridge. Current meniscal allograft implants are prepared for surgery with the bone bridge in the shape of a dovetail. Some surgeons have preference on alternative surgical technique requiring the bone bridge of the meniscal allograft to be in the shape of a rectangular slot. The device 100 described above creates a new guided approach to convert the dovetail shape of the prepared bone bridge of the meniscal allograft into a rectangular slot. As most meniscal allografts are delivered with the bone bridge portion in the shape of a dovetail, the device 100 described above may assist in inventory management since the dovetail bone bridge can easily be transformed into a rectangular bone bridge.

Thus, in use, the surgeon prepares a rectangular slot in the tibia of the patient. Next, the surgeon positions a meniscal allograft 118 with a dovetail-shaped bone bridge on the base 102 of the device 100 between the first sidewall 104 and the second sidewall 106. The locking member 110 is used to secure the meniscal allograft 118 to the device 100. The variability of the screw length of the locking member 110 accommodates all different sized allografts. Next, the surgeon positions the removable cutting guide 112 onto the device 100. Once the removable cutting guide 112 is in place, the surgeon makes a cut with a saw through the slotted through-hole 114 to trim the dovetail-shaped bone bridge of the meniscal allograft 118 into a rectangular slot. The surgeon then positions the rectangular bone bridge of the meniscal allograft 118 into the prepared rectangular slot in the tibia. Next, as the meniscal allograft is positioned, the surgeon leads the graft passing suture out the posterior lateral capsule via a standard inside/out meniscal suturing technique to thereby provide peripheral graft fixation to the capsular rim.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other examples may include more or less of each element shown in a given Figure. Further, some of the illustrated elements may be combined or omitted. Yet further, an example may include elements that are not illustrated in the Figures.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" or "an example" means that one or more feature, structure, or characteristic described in connection with the example is included in at least one implementation. The phrases "one embodiment" or "one example" or "an example" in various places in the specification may or may not be referring to the same example.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The limitations of the following claims are not written in means-plus-function format and are not intended to be interpreted based on 35 U.S.C. § 112 (f), unless and until such claim limitations expressly use the phrase "means for" followed by a statement of function void of further structure.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. For example, in one embodiment, the term "about" can refer to ±5% of a given value.

Illustrative, non-exhaustive examples, which may or may not be claimed, of the subject matter according the present disclosure are provided below.

What is claimed is:

1. A device for converting a dovetail-shaped bone bridge of a meniscal allograft into a rectangular shape, the device comprising:

a base;

a first sidewall extending vertically from the base;

a second sidewall extending vertically from the base, wherein the second sidewall is spaced away from the first sidewall at a fixed distance;

a third sidewall extending vertically from the base, wherein the third sidewall is fixedly coupled to the first sidewall and the second sidewall, wherein the base, the first sidewall, the second sidewall, and the third sidewall define a receiving volume configured to at least partially receive the dovetail-shaped bone bridge of the meniscal allograft;

a locking member coupled to the second sidewall, wherein the locking member comprises a rod that extends through the second sidewall, wherein the locking member is configured to hold the bone bridge against the first sidewall; and a removable cutting guide including a slotted through-hole, wherein the removable cutting guide is configured to be removably coupled to the first sidewall and the second sidewall, wherein the slotted through-hole at least partially defines a cutting plane parallel to the third sidewall, wherein a sloped portion of the dovetail-shaped bone bridge is positioned between the cutting plane and the third sidewall when the dovetail-shaped bone bridge is positioned within the receiving volume.

2. The device of claim 1, wherein the rod comprises a threaded rod, and wherein a rotation of the threaded rod in a first direction moves the locking member closer to the first sidewall, and wherein a rotation of the threaded rod in a second direction moves the locking member further from the first sidewall.

3. The device of claim 2, wherein a longitudinal axis of the threaded rod is offset from the slotted through-hole.

4. The device of claim 1, wherein the removable cutting guide includes a first pin configured to be positioned in a first hole in the first sidewall, and wherein the removable cutting guide includes a second pin configured to be positioned in a second hole in the second sidewall.

5. The device of claim 1, wherein the third sidewall is perpendicular to both the first sidewall and the second sidewall.

6. The device of claim 1, wherein a length of the slotted through-hole is greater than the fixed distance between the first sidewall and the second sidewall.

7. The device of claim 6, wherein the first sidewall includes a first groove, wherein the second sidewall includes a second groove, and wherein the first groove and the second groove are vertically aligned with the slotted through-hole when the removable cutting guide is removably coupled to the first sidewall and the second sidewall.

8. The device of claim 7, wherein a distance from a bottom of the first groove to a bottom of the second groove is equal to the length of the slotted through-hole.

9. The device of claim 1, wherein the base includes a third groove, and wherein the third groove is vertically aligned with the slotted through-hole when the removable cutting guide is removably coupled to the first sidewall and the second sidewall.

10. The device of claim 1, wherein the slotted through-hole comprises a first slotted through-hole, wherein the base includes a second slotted through-hole, and wherein the second slotted through-hole is vertically aligned with the first slotted through-hole when the removable cutting guide is removably coupled to the first sidewall and the second sidewall.

11. The device of claim 1, further comprising an opening opposite the third sidewall.

* * * * *